(12) United States Patent
Chandrakant et al.

(10) Patent No.: US 10,182,940 B2
(45) Date of Patent: *Jan. 22, 2019

(54) PHACOEMULSIFICATION HAND PIECE WITH INTEGRATED ASPIRATION AND IRRIGATION PUMP

(71) Applicant: Alcon Research, Ltd., Fort Worth, TX (US)

(72) Inventors: Partha Chandrakant, Irvine, CA (US); Daniel J. Wilson, Lake Forest, CA (US)

(73) Assignee: Novartis AG, Basel (CH)

( * ) Notice: Subject to any disclaimer, the term of this patent is extended or adjusted under 35 U.S.C. 154(b) by 177 days.

This patent is subject to a terminal disclaimer.

(21) Appl. No.: 15/239,409

(22) Filed: Aug. 17, 2016

(65) Prior Publication Data

US 2016/0354243 A1 Dec. 8, 2016

Related U.S. Application Data

(63) Continuation of application No. 14/050,428, filed on Oct. 10, 2013, now Pat. No. 9,445,943.

(Continued)

(51) Int. Cl.
*A61F 9/007* (2006.01)
*A61M 3/02* (2006.01)
(Continued)

(52) U.S. Cl.
CPC ....... *A61F 9/00745* (2013.01); *A61M 1/0035* (2014.02); *A61M 1/0064* (2013.01);
(Continued)

(58) Field of Classification Search
CPC ............ A61F 9/00745; A61F 9/00736; A61M 1/0058; A61M 1/0064; A61M 2205/12
See application file for complete search history.

(56) References Cited

U.S. PATENT DOCUMENTS 1,121,697 A 12/1871 Wheatland
294,334 A 2/1884 Reed et al.
(Continued)

FOREIGN PATENT DOCUMENTS

CA 2316640 A1 2/2001
CA 2649867 A1 6/2001
(Continued)

OTHER PUBLICATIONS

(Citing Office Action), Non-Final Office Action, U.S. Appl. No. 12/637,886, dated Oct. 3, 2011, 11 pages.
(Continued)

*Primary Examiner* — Kevin C Sirmons
*Assistant Examiner* — Leah Swanson (57) ABSTRACT

A method of irrigating a surgical site and aspirating fluid from the surgical site. The method includes directing a fluid through an aspiration conduit in a phacoemulsification hand piece using a vacuum pressure created from a pump in the hand piece interfacing with the aspiration conduit and directing an irrigation fluid through an irrigation conduit in the hand piece using a pressure created from the pump interfacing with the irrigation conduit. The method also includes increasing an irrigation fluid flow through the irrigation conduit by activating the pump in the hand piece, detecting a pressure associated with a surgical site using a sensor, and controlling intraocular pressure (IOP) by adjusting the pump speed based on the detected pressure.

11 Claims, 4 Drawing Sheets

Related U.S. Application Data (60) Provisional application No. 61/735,637, filed on Dec. 11, 2012.

(51) Int. Cl.
 *A61M 1/00* (2006.01)
 *A61B 17/00* (2006.01)

(52) U.S. Cl.
 CPC . *A61M 3/0258* (2013.01); *A61B 2017/00973* (2013.01); *A61B 2218/002* (2013.01); *A61B 2218/007* (2013.01); *A61M 2205/3303* (2013.01); *A61M 2205/3337* (2013.01); *A61M 2205/3344* (2013.01); *A61M 2205/50* (2013.01); *A61M 2210/0612* (2013.01)

(56) References Cited

U.S. PATENT DOCUMENTS

| | | |
|---|---|---|
| 351,159 A | 10/1886 | Brengel |
| 865,631 A | 9/1907 | Cotter |
| 1,061,142 A | 5/1913 | Tesla |
| 1,061,206 A | 5/1913 | Tesla |
| 1,874,667 A | 8/1932 | Wada |
| 2,015,123 A | 9/1935 | Pennell |
| 2,121,936 A | 6/1938 | Thomas |
| 2,386,765 A | 10/1945 | Adams et al. |
| 2,536,836 A | 1/1951 | Bowling |
| 2,623,725 A | 12/1952 | Sands |
| 2,755,816 A | 7/1956 | Collins |
| 2,987,004 A | 6/1961 | Murray |
| 3,085,589 A | 4/1963 | Sands |
| 3,191,807 A | 6/1965 | Rodrigues, Jr. |
| 3,336,942 A | 8/1967 | Keith et al. |
| 3,447,478 A | 6/1969 | Clemens |
| 3,487,784 A | 1/1970 | Rafferty et al. |
| 3,561,471 A | 2/1971 | Sands |
| 3,567,345 A | 3/1971 | Ballentine |
| 3,589,363 A | 6/1971 | Banko et al. |
| 3,693,613 A | 9/1972 | Kelman |
| 3,724,974 A | 4/1973 | Molimard |
| 3,756,270 A | 9/1973 | Fonseca et al. |
| 3,784,323 A | 1/1974 | Sausse |
| 3,818,913 A | 6/1974 | Wallach |
| 3,882,872 A | 5/1975 | Douvas et al. |
| 3,930,505 A | 1/1976 | Wallach |
| 3,996,935 A | 12/1976 | Banko |
| 4,140,118 A | 2/1979 | Jassawalla |
| 4,187,057 A | 2/1980 | Xanthopoulos |
| 4,205,948 A | 6/1980 | Jones |
| 4,255,081 A | 3/1981 | Oklejas et al. |
| 4,392,794 A | 7/1983 | Foxcroft |
| 4,405,289 A | 9/1983 | Nakashima |
| 4,417,856 A | 11/1983 | Minissian |
| 4,479,761 A | 10/1984 | Bilstad et al. |
| 4,493,706 A | 1/1985 | Borsanyi et al. |
| 4,496,342 A | 1/1985 | Banko |
| 4,530,647 A | 7/1985 | Uno |
| 4,537,561 A | 8/1985 | Xanthopoulos |
| 4,657,490 A | 4/1987 | Abbott |
| 4,661,093 A | 4/1987 | Beck et al. |
| 4,684,328 A | 8/1987 | Murphy |
| 4,705,500 A | 11/1987 | Reimels et al. |
| 4,713,051 A | 12/1987 | Steppe et al. |
| 4,758,238 A | 7/1988 | Sundblom et al. |
| 4,764,165 A | 8/1988 | Reimels et al. |
| 4,768,547 A | 9/1988 | Danby et al. |
| 4,790,726 A | 12/1988 | Balkau et al. |
| 4,798,580 A | 1/1989 | Demeo et al. |
| 4,838,865 A | 6/1989 | Flank et al. |
| 4,854,825 A | 8/1989 | Bez et al. |
| 4,861,332 A | 8/1989 | Parisi |
| 4,904,238 A | 2/1990 | Williams |
| 4,909,710 A | 3/1990 | Kaplan et al. |
| 4,909,713 A | 3/1990 | Finsterwald et al. |
| 4,921,477 A | 5/1990 | Davis |
| 4,923,375 A | 5/1990 | Ejlersen |
| 4,935,005 A | 6/1990 | Haines |
| 4,963,131 A | 10/1990 | Wortrich |
| 5,038,965 A | 8/1991 | Cater |
| 5,041,096 A | 8/1991 | Beuchat et al. |
| 5,044,902 A | 9/1991 | Malbec |
| 5,046,486 A | 9/1991 | Grulke et al. |
| 5,062,775 A | 11/1991 | Orth |
| 5,106,366 A | 4/1992 | Steppe |
| 5,106,367 A | 4/1992 | Ureche et al. |
| 5,167,620 A | 12/1992 | Ureche et al. |
| 5,185,002 A | 2/1993 | Venturini |
| 5,195,960 A | 3/1993 | Hossain et al. |
| 5,207,647 A | 5/1993 | Phelps |
| 5,257,917 A | 11/1993 | Minarik et al. |
| 5,263,830 A | 11/1993 | Goi et al. |
| 5,267,956 A | 12/1993 | Beuchat |
| 5,273,517 A | 12/1993 | Barone et al. |
| 5,302,093 A | 4/1994 | Owens et al. |
| 5,316,440 A | 5/1994 | Kijima et al. |
| 5,342,181 A | 8/1994 | Schock et al. |
| 5,350,357 A | 9/1994 | Kamen et al. |
| 5,364,342 A | 11/1994 | Beuchat et al. |
| 5,392,653 A | 2/1995 | Zanger et al. |
| 5,403,277 A | 4/1995 | Dodge et al. |
| 5,429,485 A | 7/1995 | Dodge |
| 5,429,601 A | 7/1995 | Conley et al. |
| 5,429,602 A | 7/1995 | Hauser |
| 5,443,370 A | 8/1995 | Wang |
| 5,460,490 A | 10/1995 | Carr et al. |
| 5,462,416 A | 10/1995 | Dennehey et al. |
| 5,470,312 A | 11/1995 | Zanger et al. |
| 5,476,448 A | 12/1995 | Urich |
| 5,484,239 A | 1/1996 | Chapman et al. |
| 5,487,747 A | 1/1996 | Stagmann et al. |
| 5,515,930 A | 5/1996 | Glaser |
| 5,518,378 A | 5/1996 | Neftel et al. |
| 5,533,976 A | 7/1996 | Zaleski et al. |
| 5,542,918 A | 8/1996 | Atkinson |
| 5,554,013 A | 9/1996 | Owens et al. |
| 5,575,632 A | 11/1996 | Morris et al. |
| 5,588,815 A | 12/1996 | Zaleski, II |
| 5,630,711 A | 5/1997 | Luedtke et al. |
| 5,674,226 A | 10/1997 | Doherty et al. |
| 5,688,112 A | 11/1997 | Garay |
| 5,697,910 A | 12/1997 | Cole et al. |
| 5,705,018 A | 1/1998 | Hartley |
| 5,709,539 A | 1/1998 | Hammer et al. |
| 5,712,543 A | 1/1998 | Sjostrom |
| 5,733,256 A | 3/1998 | Costin |
| 5,746,708 A | 5/1998 | Giesler et al. |
| 5,746,719 A | 5/1998 | Farra et al. |
| 5,759,017 A | 6/1998 | Patton et al. |
| 5,782,634 A | 7/1998 | Lingenhöle et al. |
| 5,788,667 A | 8/1998 | Stoller |
| 5,810,765 A | 9/1998 | Oda |
| 5,827,218 A | 10/1998 | Nguyen et al. |
| 5,853,386 A | 12/1998 | Davis et al. |
| 5,879,363 A | 3/1999 | Urich |
| 5,897,300 A | 4/1999 | Luedtke |
| 5,897,524 A | 4/1999 | Wortrich et al. |
| 5,906,598 A | 5/1999 | Giesler et al. |
| 5,910,110 A | 6/1999 | Bastable |
| 5,927,956 A | 7/1999 | Lim et al. |
| 5,951,581 A | 9/1999 | Saadat et al. |
| 5,972,012 A | 10/1999 | Ream et al. |
| 5,989,212 A | 11/1999 | Sussman et al. |
| 5,996,634 A | 12/1999 | Dennehey et al. |
| 5,997,499 A | 12/1999 | Sussman et al. |
| 6,012,999 A | 1/2000 | Patterson |
| 6,042,586 A | 3/2000 | Kawano et al. |
| 6,058,779 A | 5/2000 | Cole |
| 6,080,128 A | 6/2000 | Sussman et al. |
| 6,109,895 A | 8/2000 | Ray et al. |
| 6,110,162 A | 8/2000 | Sussman et al. |
| 6,117,149 A | 9/2000 | Sorensen et al. |
| 6,129,699 A | 10/2000 | Haight et al. |
| 6,179,805 B1 | 1/2001 | Sussman et al. |

(56) References Cited

U.S. PATENT DOCUMENTS

| | | |
|---|---|---|
| 6,217,543 B1 | 4/2001 | Anis et al. |
| 6,241,700 B1 | 6/2001 | Leukanech |
| 6,270,326 B1 | 8/2001 | Kuriyama |
| 6,293,926 B1 | 9/2001 | Sorensen et al. |
| 6,296,460 B1 | 10/2001 | Smith |
| 6,416,293 B1 | 7/2002 | Bouchard et al. |
| 6,432,078 B1 | 8/2002 | Peyman |
| 6,491,661 B1 | 12/2002 | Boukhny et al. |
| 6,527,765 B2 | 3/2003 | Kelman et al. |
| 6,551,080 B2 | 4/2003 | Andersen et al. |
| 6,572,349 B2 | 6/2003 | Sorensen et al. |
| 6,599,277 B2 | 7/2003 | Neubert |
| 6,605,054 B2 | 8/2003 | Rockley |
| 6,655,934 B2 | 12/2003 | Mittelstein et al. |
| 6,689,146 B1 | 2/2004 | Himes |
| 6,723,065 B2 | 4/2004 | Kishimoto |
| 6,749,403 B2 | 6/2004 | Bryant et al. |
| 6,811,386 B2 | 11/2004 | Hedington et al. |
| 6,814,547 B2 | 11/2004 | Childers et al. |
| 6,868,987 B2 | 3/2005 | Hedington et al. |
| 6,958,058 B1 | 10/2005 | Hunter, Sr. et al. |
| 6,962,488 B2 | 11/2005 | Davis et al. |
| 7,063,688 B2 | 6/2006 | Say |
| 7,070,574 B2 | 7/2006 | Jackson et al. |
| 7,144,383 B2 | 12/2006 | Arnett et al. |
| 7,150,607 B2 | 12/2006 | Pelmulder et al. |
| 7,238,164 B2 | 7/2007 | Childers et al. |
| 7,273,359 B2 | 9/2007 | Blight et al. |
| 7,276,060 B2 | 10/2007 | Madden |
| 7,393,189 B2 | 7/2008 | Davis et al. |
| 7,445,436 B2 | 11/2008 | Mittelstein et al. |
| 7,540,855 B2 | 6/2009 | Lumpkin et al. |
| 7,604,610 B2 | 10/2009 | Shener et al. |
| 7,632,080 B2 | 12/2009 | Tracey et al. |
| 7,645,127 B2 | 1/2010 | Hagen et al. |
| 7,695,242 B2 | 4/2010 | Fuller |
| 7,758,515 B2 | 7/2010 | Hibner |
| 7,775,780 B2 | 8/2010 | Hopkins et al. |
| 7,862,540 B2 | 1/2011 | Dacquay et al. |
| 7,967,777 B2 | 6/2011 | Edwards et al. |
| 8,070,712 B2 | 12/2011 | Muri et al. |
| 8,087,909 B2 | 1/2012 | Shener |
| 8,162,633 B2 | 4/2012 | Edwards |
| 8,366,420 B1 | 2/2013 | Geschwender |
| 8,579,929 B2 | 11/2013 | Mackool et al. |
| 8,617,106 B2 | 12/2013 | Zacharias |
| 2001/0016706 A1 | 8/2001 | Leukanech et al. |
| 2002/0058914 A1 | 5/2002 | Henniges et al. |
| 2002/0062105 A1 | 5/2002 | Tanner et al. |
| 2002/0077587 A1 | 6/2002 | Boukhny et al. |
| 2003/0108429 A1 | 6/2003 | Angelini et al. |
| 2003/0199803 A1 | 10/2003 | Robinson et al. |
| 2004/0122381 A1 | 6/2004 | Arnold |
| 2004/0253129 A1 | 12/2004 | Sorensen et al. |
| 2005/0049539 A1 | 3/2005 | O'Hara, Jr. et al. |
| 2005/0070859 A1 | 3/2005 | Cull et al. |
| 2005/0100450 A1 | 5/2005 | Bryant et al. |
| 2005/0271531 A1 | 12/2005 | Brown, Jr. et al. |
| 2006/0000925 A1 | 1/2006 | Maher et al. |
| 2006/0093989 A1 | 5/2006 | Hahn et al. |
| 2006/0110274 A1 | 5/2006 | Gottschalk |
| 2006/0122556 A1 | 6/2006 | Kumar et al. |
| 2006/0245964 A1 | 11/2006 | Koslov |
| 2006/0253194 A1 | 11/2006 | Dial |
| 2007/0078370 A1 | 4/2007 | Shener et al. |
| 2007/0078379 A1 | 4/2007 | Boukhny et al. |
| 2007/0100316 A1 | 5/2007 | Traxinger |
| 2007/0135760 A1 | 6/2007 | Williams |
| 2007/0217919 A1 | 9/2007 | Gordon et al. |
| 2007/0278155 A1 | 12/2007 | Lo et al. |
| 2007/0287959 A1 | 12/2007 | Walter et al. |
| 2008/0097320 A1 | 4/2008 | Moore et al. |
| 2008/0112828 A1 | 5/2008 | Muri et al. |
| 2008/0114289 A1 | 5/2008 | Muri et al. |
| 2008/0114291 A1 | 5/2008 | Muri et al. |
| 2008/0114301 A1 | 5/2008 | Bandhauer et al. |
| 2008/0114311 A1 | 5/2008 | Muri et al. |
| 2008/0114312 A1 | 5/2008 | Muri et al. |
| 2008/0114372 A1 | 5/2008 | Edwards et al. |
| 2008/0200878 A1 | 8/2008 | Davis et al. |
| 2008/0220092 A1 | 9/2008 | Dipierro et al. |
| 2008/0240951 A1 | 10/2008 | Domash et al. |
| 2008/0247892 A1 | 10/2008 | Kawasumi |
| 2009/0012460 A1 | 1/2009 | Steck et al. |
| 2009/0035164 A1 | 2/2009 | Edwards |
| 2009/0060756 A1 | 3/2009 | Jones |
| 2009/0084718 A1 | 4/2009 | Prisco et al. |
| 2009/0149802 A1 | 6/2009 | Jones |
| 2009/0246035 A1 | 10/2009 | Patzer |
| 2009/0299272 A1 | 12/2009 | Hopping et al. |
| 2009/0317271 A1 | 12/2009 | Gill et al. |
| 2010/0125257 A1 | 5/2010 | Perkins et al. |
| 2010/0130920 A1 | 5/2010 | Lo et al. |
| 2010/0130934 A1 | 5/2010 | Rochat |
| 2010/0145259 A1 | 6/2010 | Nash et al. |
| 2010/0191178 A1 | 7/2010 | Ross et al. |
| 2010/0228146 A1 | 9/2010 | Hibner |
| 2010/0241044 A1 | 9/2010 | Caleffi et al. |
| 2010/0280435 A1 | 11/2010 | Raney et al. |
| 2010/0286791 A1 | 11/2010 | Goldsmith |
| 2011/0092891 A1 | 4/2011 | Gerg et al. |
| 2011/0137231 A1 | 6/2011 | Sorensen et al. |
| 2011/0144567 A1 | 6/2011 | Sorensen et al. |
| 2011/0184374 A1 | 7/2011 | Gao et al. |
| 2011/0313343 A1 | 12/2011 | Milutinovic et al. |
| 2012/0041358 A1 | 2/2012 | Mann et al. |
| 2012/0065578 A1 | 3/2012 | Zhou |
| 2012/0080108 A1 | 4/2012 | Arnold |
| 2012/0083728 A1 | 4/2012 | Sorensen et al. |
| 2013/0274775 A1 | 10/2013 | Dexter et al. |

FOREIGN PATENT DOCUMENTS

| | | |
|---|---|---|
| CA | 2649867 C | 6/2001 |
| CA | 2743969 A1 | 3/2005 |
| CN | 1214903 A | 4/1999 |
| CN | 1686067 A | 10/2005 |
| CN | 101023898 | 8/2007 |
| CN | 200991440 Y | 12/2007 |
| DE | 3809582 A1 | 10/1989 |
| DE | 19749358 A1 | 5/1998 |
| DE | 19711675 A1 | 10/1998 |
| DE | 19856744 A1 | 6/2000 |
| DE | 10034711 A1 | 2/2002 |
| DE | 10034711 B4 | 4/2006 |
| DE | 102007044790 A1 | 4/2009 |
| EP | 0200448 A3 | 11/1986 |
| EP | 0320963 A2 | 6/1989 |
| EP | 0362822 A2 | 4/1990 |
| EP | 0518050 A1 | 12/1992 |
| EP | 0518050 B1 | 7/1996 |
| EP | 0731275 A1 | 9/1996 |
| EP | 0964711 B1 | 12/1999 |
| EP | 1140257 B1 | 7/2002 |
| EP | 1258260 A2 | 11/2002 |
| EP | 0944404 B1 | 6/2006 |
| EP | 1779825 A2 | 5/2007 |
| EP | 1810702 A1 | 7/2007 |
| EP | 2365220 A1 | 9/2011 |
| EP | 1847711 B1 | 11/2011 |
| EP | 2509659 B1 | 1/2015 |
| FR | 2466641 | 4/1981 |
| FR | 2797190 A1 | 2/2001 |
| GB | 2029514 | 3/1980 |
| GB | 2174763 A | 11/1986 |
| GB | 2190145 | 11/1987 |
| JP | 360001391 A | 1/1985 |
| JP | 63290564 | 11/1988 |
| JP | 02070987 | 3/1990 |
| JP | H03164586 | 7/1991 |
| JP | 2002248117 | 9/2002 |
| JP | 3785643 | 6/2006 |
| JP | 2007507636 | 3/2007 |
| JP | 2007198382 | 8/2007 |

(56) References Cited

FOREIGN PATENT DOCUMENTS

| | | |
|---|---|---|
| JP | 2007247646 | 9/2007 |
| JP | 2008546501 | 12/2008 |
| RU | 2197277 | 1/2003 |
| RU | 2241887 | 12/2004 |
| SU | 1533696 | 1/1990 |
| SU | 1590649 | 9/1990 |
| WO | 9517597 | 6/1995 |
| WO | 9818507 | 5/1998 |
| WO | 9824495 | 6/1998 |
| WO | 9938549 | 8/1999 |
| WO | 0022995 | 4/2000 |
| WO | 0033898 | 6/2000 |
| WO | 0053136 | 9/2000 |
| WO | 03073969 | 9/2003 |
| WO | 2005009511 A2 | 2/2005 |
| WO | 2005009511 A3 | 6/2005 |
| WO | 2008131357 | 10/2008 |
| WO | 2009005900 | 1/2009 |
| WO | 2009036818 A1 | 3/2009 |
| WO | 2009146913 A2 | 12/2009 |
| WO | 2009146913 A3 | 2/2010 |
| WO | 2010061863 | 6/2010 |
| WO | 2010129128 | 11/2010 |
| WO | 2011/075332 A1 | 6/2011 |
| WO | 2011071775 | 6/2011 |
| WO | 2011140167 | 11/2011 |
| WO | 2011/159428 A1 | 12/2011 |
| WO | 2012048261 A2 | 4/2012 |
| WO | 2012048261 A3 | 6/2012 |

OTHER PUBLICATIONS

European Patent Office, Extended European Search Report for Application No. EP 14768258.7, Publication No. EP2941565, Published Nov. 11, 2015, dated Mar. 8, 2016, 8 pages.
European Patent Office, Supplementary European Search Report for Application No. EP 10836456.3, Publication No. EP 2509659, Published Oct. 17, 2012, dated Mar. 20, 2013, 5 pages.
European Patent Office, Supplementary European Search Report for Application No. EP 10838118.7, Publication No. EP2512554, Published Oct. 24, 2012, dated Apr. 25, 2013, 7 pages.
http://www.advancedfluid.com/discflo/concepts.htm. Web archive dated Aug. 7, 2008, 3 pages.
International Searching Authority, International Search Report, PCT/US2014/61397, dated Jan. 29, 2015, 2 pgs.
International Searching Authority, International Preliminary Report on Patentability and Written Opinion issued for PCT/US2010/058931, dated Jun. 12, 2012, 5 pages.
International Searching Authority, International Preliminary Report on Patentability and Written Opinion, International Application No. PCT/US2014/027271, dated Sep. 15, 2015, 6 pages.
International Searching Authority, International Preliminary Report on Patentability and Written Opinion, International Application No. PCT/US2014/027307, dated Sep. 15, 2015, 5 pages.
International Searching Authority, International Preliminary Report on Patentability and Written Opinion, issued for International Application No. PCT/US2010/059032, dated Jun. 19, 2012, 6 pages.
International Searching Authority, International Report on Patentability and Written Opinion, International Application No. PCT/US2014/027233, dated Sep. 15, 2015, 8 pages.
International Searching Authority, International Search Report and Written Opinion issued for PCT/US2014/064416 dated Feb. 18, 2015, 9 pages.
International Searching Authority, International Search Report and Written Opinion, International Application No. PCT/US2014/027233, filed Mar. 14, 2014, dated Jul. 31, 2014, 10 pages.
International Searching Authority, International Search Report and Written Opinion, International Application No. PCT/US2014/027271, filed Mar. 14, 2014, dated Jul. 28, 2014, 8 pages.
International Searching Authority, International Search Report and Written Opinion, International Application No. PCT/US2014/027307, filed Mar. 14, 2014, dated Jul. 30, 2014, 7 pages.
International Searching Authority, International Search Report and Written Opinion, International Application No. PCT/US2015/026293, dated Jul. 23, 2015, 11 pages.
International Searching Authority, International Search Report for PCT/US2010/058931, filed Dec. 3, 2010, Publication No. 2011071775, Published Jun. 16, 2011, dated Feb. 1, 2011, 2 pages.
International Searching Authority, International Search Report for PCT/US2010/059032, filed Dec. 5, 2010, Publication No. 2011075332, Published Jun. 23, 2011, dated Jan. 31, 2011, 2 pages.
International Searching Authority, International Search Report, PCT/US2010/041786, dated Oct. 28, 2010, 5 pages.
International Searching Authority, International Search Report, PCT/US2015/037783, dated Sep. 28, 2015, 4 pages.
International Searching Authority, Written Opinion, International Application No. PCT/US2010/030168, dated Aug. 3, 2010, 8 pages.
International Searching Authority, Written Opinion, International Application No. PCT/US2010/058931, dated Feb. 1, 2011, 4 pages.
International Searching Authority, Written Opinion, International Application No. PCT/US2010/059032, dated Jan. 31, 2011, 5 pages.
International Searching Authority, Written Opinion, PCT/US2009/057675, dated Mar. 25, 2011, 5 pages.
International Searching Authority, Written Opinion, PCT/US2010/041786, dated Oct. 28, 2010, 6 pages.
International Searching Authority, Written Opinion, PCT/US2015/037783, dated Sep. 28, 2015, 5 pages.
Kishimoto, Makoto, MD, OPESAVER—Super Irrigation System, Techniques in Ophthalmology, 2006, 6 pages, vol. 4, Issue 1, Lippincott Williams & Wilkins, Shiga, Japan.
Milutinovic, et al., "Phacoemulsification Fluidics System Having a Single Pump Head," U.S. Appl. No. 12/818,682, filed Jun. 18, 2010, 28 pages.
Ovchinnikov et al., Acoustic Streaming of a Sharp Edge, Journal of Acoustical Society of America, 136 (1), Jul. 2014, pp. 22-29.
Sorensen, Gary, Phacoemulsification Hand Piece with Integrated Aspiration Pump, U.S. Appl. No. 13/325,549, filed Dec. 14, 2011, 18 pages.
European Patent Office, Extended European Search Report, Application No. 13863111.4, dated Jul. 14, 2015, 6 pgs.
International Searching Authority, International Preliminary Report on Patentability, PCT/US2013/064202, dated Jun. 16, 2015.
International Searching Authority, International Search Report, PCT/US2013/064202, dated Jan. 10, 2014, 2 pages.
International Searching Authority, Written Opinion, PCT/US2013/064202, dated Jan. 10, 2014., 5 pages.

PHACOEMULSIFICATION HAND PIECE WITH INTEGRATED ASPIRATION AND IRRIGATION PUMP

BACKGROUND

The devices, system, and methods disclosed herein relate generally to phacoemulsification surgery, and more particularly, to a device that better regulates pressure experienced in the eye during cataract surgery.

The human eye functions to provide vision by transmitting light through a clear outer portion called the cornea, and focusing the image by way of a crystalline lens onto a retina. The quality of the focused image depends on many factors including the size and shape of the eye, and the transparency of the cornea and the lens. When age or disease causes the lens to become less transparent, vision deteriorates because of the diminished light which can be transmitted to the retina. This deficiency in the lens of the eye is medically known as a cataract. An accepted treatment for this condition is surgical removal of the lens and replacement of the lens function by an artificial intraocular lens (IOL).

In the United States, the majority of cataractous lenses are removed by a surgical technique called phacoemulsification. A typical surgical hand piece suitable for phacoemulsification procedures consists of an ultrasonically driven phacoemulsification hand piece, an attached hollow cutting needle surrounded by an irrigating sleeve, and an electronic control console. The hand piece assembly is attached to the control console by an electric cable and flexible conduit. Through the electric cable, the console varies the power level transmitted by the hand piece to the attached cutting needle. The flexible conduit supplies irrigation fluid to the surgical site and draws aspiration fluid from the eye through the hand piece assembly.

The operative part in a typical hand piece is a centrally located, hollow resonating bar or horn directly attached to a set of piezoelectric crystals. The crystals supply the required ultrasonic vibration needed to drive both the horn and the attached cutting needle during phacoemulsification, and are controlled by the console. The crystal/horn assembly is suspended within the hollow body or shell of the hand piece by flexible mountings. The hand piece body terminates in a reduced diameter portion or nosecone at the body's distal end. Typically, the nosecone is externally threaded to accept the hollow irrigation sleeve, which surrounds most of the length of the cutting needle. Likewise, the horn bore is internally threaded at its distal end to receive the external threads of the cutting tip. The irrigation sleeve also has an internally threaded bore that is screwed onto the external threads of the nosecone. The cutting needle is adjusted so that its tip projects only a predetermined amount past the open end of the irrigating sleeve.

During the phacoemulsification procedure, the tip of the cutting needle and the end of the irrigation sleeve are inserted into the anterior segment of the eye through a small incision in the outer tissue of the eye. The surgeon brings the tip of the cutting needle into contact with the lens of the eye, so that the vibrating tip fragments the lens. The resulting fragments are aspirated out of the eye through the interior bore of the cutting needle, along with irrigation solution provided to the eye during the procedure, and into a drain reservoir.

Throughout the procedure, irrigating fluid is pumped into the eye, passing between the irrigation sleeve and the cutting needle and exiting into the eye at the tip of the irrigation sleeve and/or from one or more ports, or openings, cut into the irrigation sleeve near its end. This irrigating fluid is critical, as it prevents the collapse of the eye during the removal of the emulsified lens. The irrigating fluid also protects the eye tissues from the heat generated by the vibrating of the ultrasonic cutting needle. Furthermore, the irrigating fluid suspends the fragments of the emulsified lens for aspiration from the eye.

A common phenomenon during a phacoemulsification procedure arises from the varying flow rates that occur throughout the surgical procedure. Varying flow rates result in varying pressure losses in the irrigation fluid path from the irrigation fluid supply to the eye, thus causing changes in pressure in the anterior chamber (also referred to as Intra-Ocular Pressure or IOP.) Higher flow rates result in greater pressure losses and lower IOP. As IOP lowers, the operating space within the eye diminishes.

Another common complication during the phacoemulsification process arises from a blockage, or occlusion, of the aspirating needle. As the irrigation fluid and emulsified tissue is aspirated away from the interior of the eye through the hollow cutting needle, pieces of tissue that are larger than the diameter of the needle's bore may become clogged in the needle's tip. While the tip is clogged, vacuum pressure builds up within the tip. The resulting drop in pressure in the anterior chamber in the eye when the clog is removed is known as post-occlusion surge. This post-occlusion surge can, in some cases, cause a relatively large quantity of fluid and tissue to be aspirated out of the eye too quickly, potentially causing the eye to collapse and/or causing the lens capsule to be torn.

Various techniques have been designed to reduce this surge. However, there remains a need for improved phacoemulsification devices that reduce post-occlusion surge as well as maintain a stable IOP throughout varying flow conditions. Eliminating the need for complex active irrigation systems and reducing the number of required devices is also needed. The present disclosure addresses one or more deficiencies in the prior art.

SUMMARY

In an exemplary aspect, the present disclosure is directed a phacoemulsification hand piece. The hand piece includes a body having a distal end and a proximal end, an ultrasonic tip disposed at the distal end of the body and configured to aspirate an aspiration fluid from a surgical site, and a sleeve disposed at the distal end of the body configured to irrigate the surgical site with an irrigation fluid. The hand piece also includes a removable cartridge disposed in the body and in fluid communication with the ultrasonic tip and the sleeve, wherein the cartridge comprises an aspiration conduit configured to contain the aspiration fluid and an irrigation conduit configured to contain the irrigation fluid. The hand piece also includes a pump disposed within the body and interfacing with the aspiration conduit and with the irrigation conduit, such that upon activation of the pump, the irrigation fluid within the irrigation conduit flows in a direction towards the sleeve and away from the proximal end, and the aspiration fluid within the aspiration conduit flows in a direction away from the tip and towards the proximal end.

In an aspect, the hand piece also includes a valve disposed within the body and configured to interface with the aspiration conduit, the valve configured to control a flow rate of aspiration fluid within the aspiration conduit.

In another exemplary aspect, the present disclosure is directed to a method of irrigating a surgical site and aspirating fluid from the surgical site. The method includes directing a fluid through an aspiration conduit in a phacoemulsification hand piece using a vacuum pressure created from a pump in the hand piece interfacing with the aspiration conduit and directing an irrigation fluid through an irrigation conduit in the hand piece using a pressure created from the pump interfacing with the irrigation conduit. The method also includes increasing an irrigation fluid flow through the irrigation conduit by activating the pump in the hand piece, detecting a pressure associated with a surgical site using a sensor, and controlling intraocular pressure (IOP) by adjusting the state of an aspiration valve based on the detected pressure.

In an aspect, the method includes controlling IOP by adjusting a pump speed based on the pressure.

In another exemplary aspect, the present disclosure is directed to an aspiration and irrigation system for irrigating the eye and aspirating fluid from the eye during an ocular surgery. The system includes a phacoemulsification hand piece comprising a graspable body having a distal end and a proximal end, an aspiration conduit configured to transport an aspiration fluid away from a surgical site, and an irrigation conduit configured to transport an irrigation fluid towards the surgical site. The system also includes a pump disposed within the hand piece, wherein at least a portion of the pump interfaces with the aspiration conduit and the irrigation conduit, such that upon activation of the pump, the irrigation fluid within the irrigation conduit flows in a direction towards the surgical site, and the aspiration fluid within the aspiration conduit flows in a direction away from the surgical site. The system also includes a valve disposed within the hand piece configured to interface with the aspiration conduit, the valve configured to control a flow rate of aspiration fluid within the aspiration conduit. The system also includes a sensor detecting pressure representative of a surgical site pressure and a controller in communication with the pump, the valve, and the sensor, wherein the controller is configured to control the operation of the pump and the valve based on information from the sensor, and wherein the controller is configured to change intraocular pressure (IOP) at the surgical site.

In an aspect, the controller is configured to change IOP by adjusting the pump speed or by adjusting the state of the valve or both.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

The accompanying drawings illustrate embodiments of the devices and methods disclosed herein and together with the description, serve to explain the principles of the present disclosure.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately. For simplicity, in some instances the same reference numbers are used throughout the drawings to refer to the same or like parts.

The present disclosure relates generally to devices, systems, and methods for phacoemulsification procedures. Maintaining the IOP within a predetermined range during phacoemulsification may be important to the success of the procedure. The flow of irrigation fluid into the surgical site and the flow of aspiration fluid out of the surgical site are two significant factors affecting the IOP. Early detection and correction of any changes to the irrigation fluid flow or aspiration fluid flow greatly improves the stability of the IOP.

The devices, system, and methods disclosed herein include a hand piece with an integrated aspiration and irrigation pump and an aspiration valve designed to quickly change the aspiration flow and irrigation flow. In the embodiment disclosed herein, the use of one pump located in the hand piece to control both the irrigation flow and aspiration flow allows for quick adjustments to flow while maintaining a graspable hand piece body size. In some embodiments, the hand piece includes a sensor detecting IOP information at the surgical site. This allows for the early detection of IOP changes.

Figure 1:
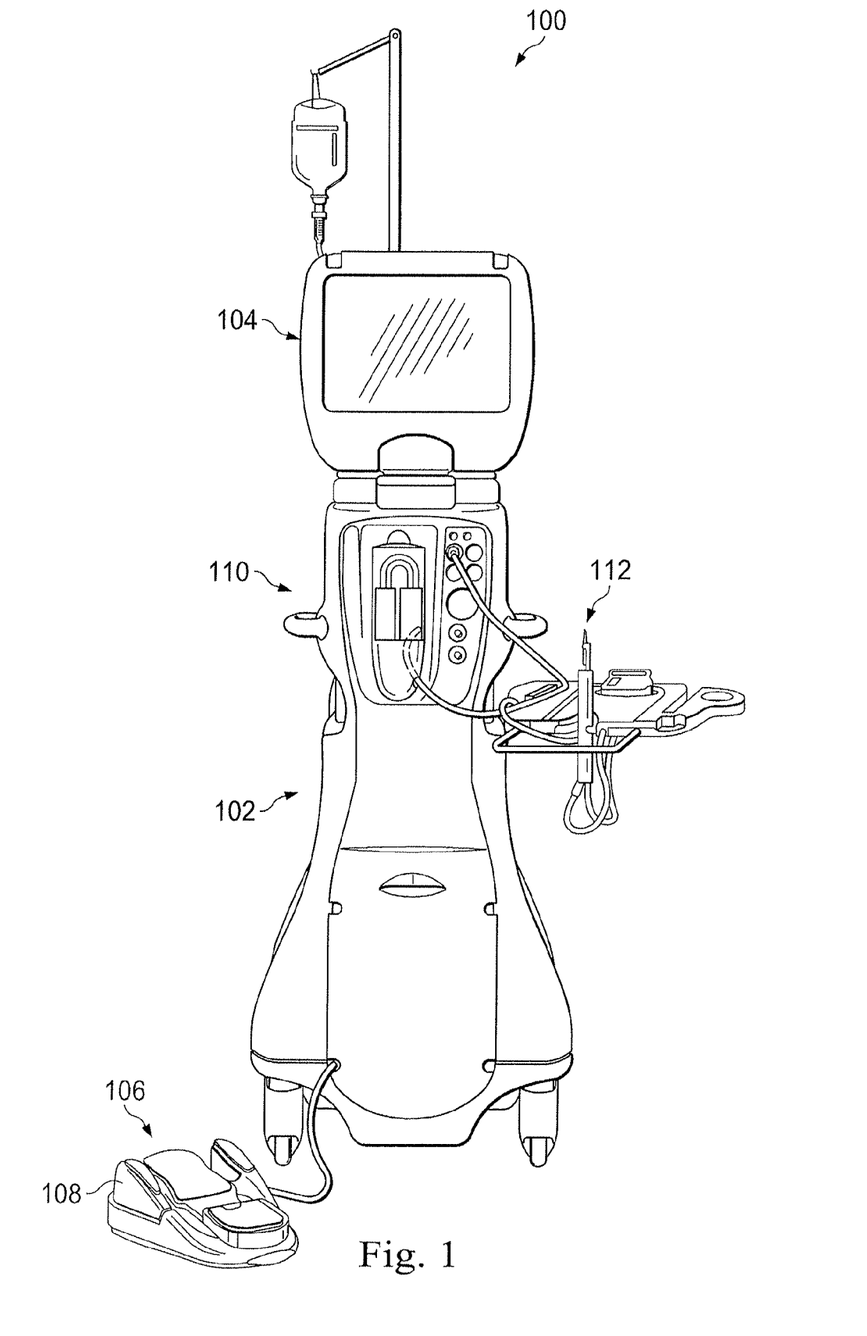
FIG. 1 is an illustration of an exemplary phacoemulsification surgical console according to an embodiment consistent with the principles of the present disclosure.
Figure 2:
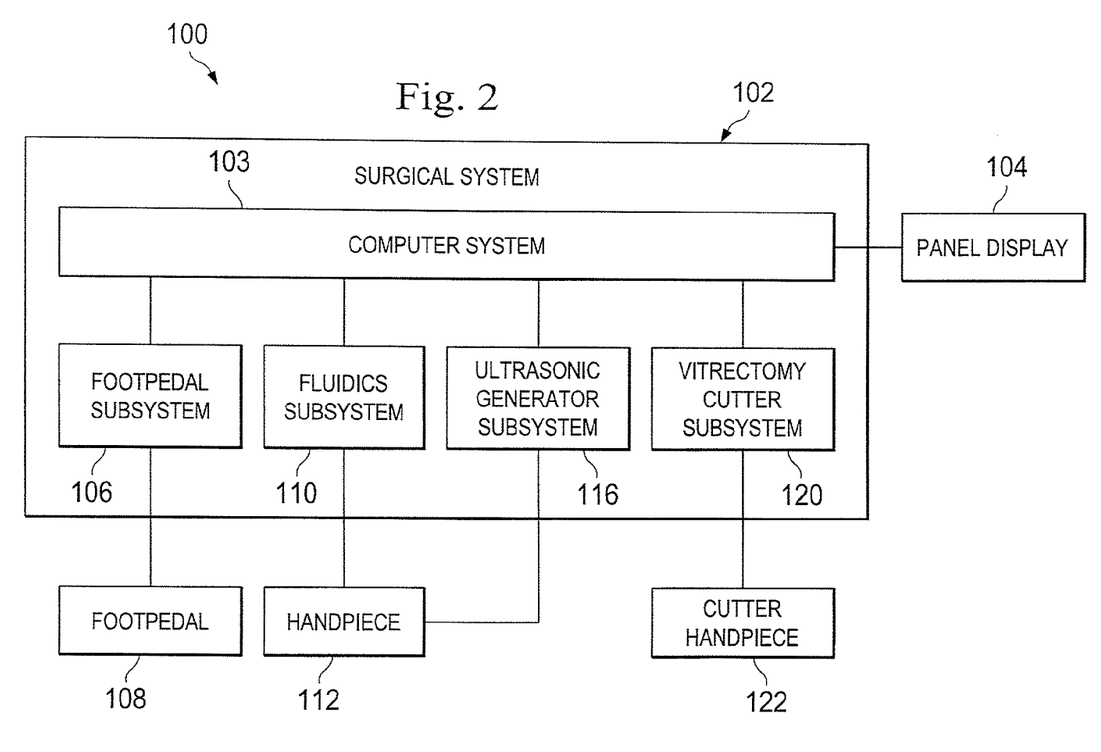
FIG. 2 is a block diagram of the phacoemulsification console of FIG. 1 showing various subsystems including a fluidics subsystem that drives aspiration and irrigation according to an embodiment consistent with the principles of the present disclosure.

FIG. 1 illustrates an exemplary emulsification surgical console, generally designated 100. FIG. 2 is a block diagram of the console 100 showing various subsystems that operate to perform a phacoemulsification procedure. The console 100 includes a base housing 102 with a computer system 103 and an associated display screen 104 showing data relating to system operation and performance during a phacoemulsification surgical procedure. The console 100 also includes at least a part of a number of subsystems that are used together to perform an emulsification surgical procedure. Some of these subsystems include components or elements that are separable from or not disposed on the console 100. For example, the subsystems include a foot pedal subsystem 106 that includes, for example, a foot pedal 108, a fluidics subsystem 110 including a hand piece 112 with an integrated aspiration and irrigation pump, an ultrasonic generator subsystem 116 that provides an ultrasonic oscillation to a cutting needle of the hand piece 112, and a pneumatic vitrectomy cutter subsystem 120 including a vitrectomy hand piece 122 (not shown in FIG. 1). These subsystems may overlap and cooperate to perform various aspects of the procedure.

Figure 3:
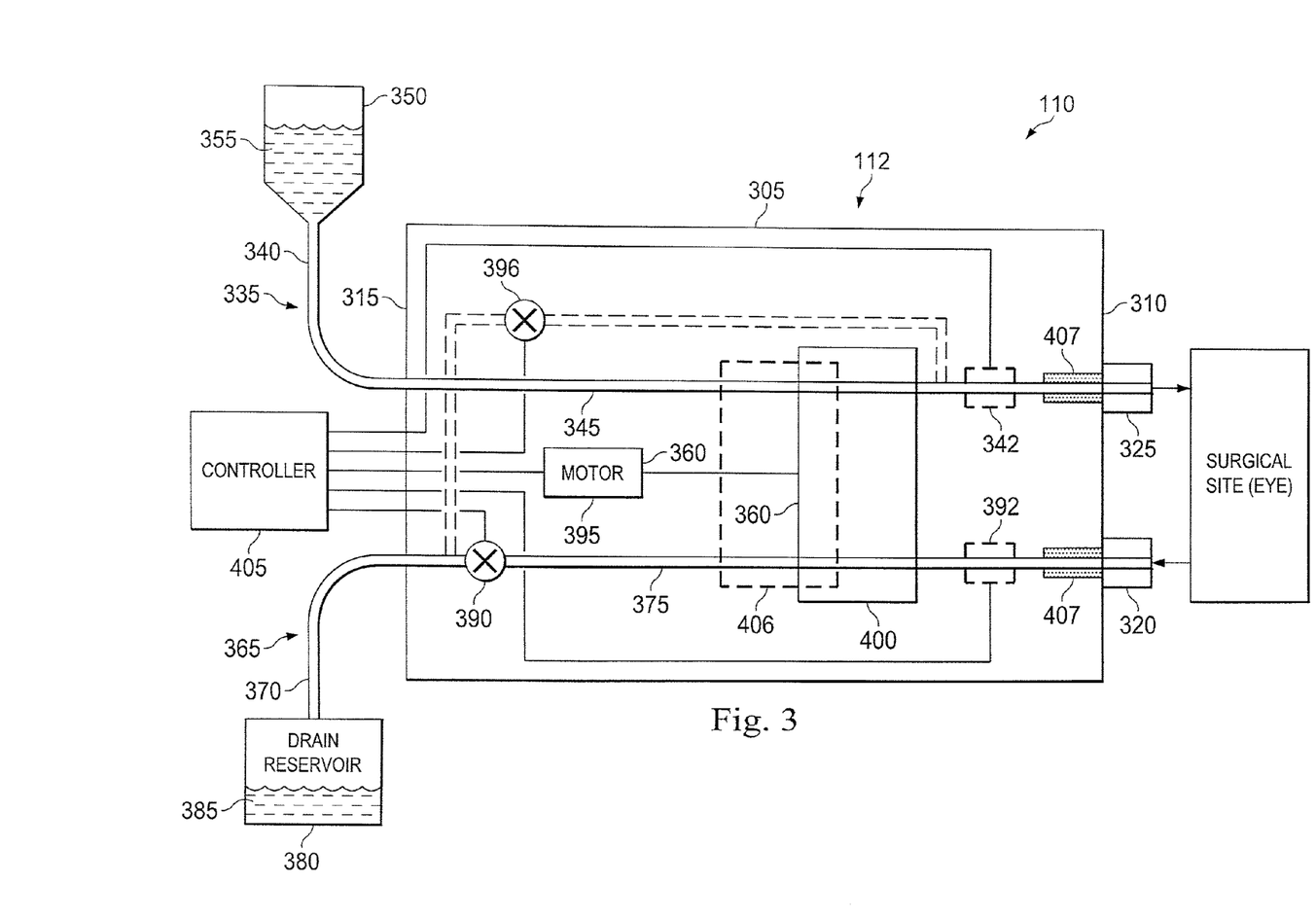
FIG. 3 is a block diagram of a part of the fluidics subsystem of FIG. 2 with a phacoemulsification hand piece having an integrated pump according to an embodiment consistent with the principles of the present disclosure.

FIG. 3 is a block diagram schematically illustrating a part of the fluidics subsystem 110 according to an exemplary embodiment. The fluidics subsystem 110 includes an irrigation system 335, an aspiration system 365, and the hand piece 112. In FIG. 3, hand piece 112 comprises a graspable body 305 having a distal end denoted by number 310 and a proximal end denoted by number 315. A cutting tip 320 and an irrigation sleeve 325 extend from the distal end 310 and are in fluid communication with a surgical site, such as an eye during a phacoemulsification procedure. In FIG. 3, the cutting up 320 and the irrigation sleeve 325 are shown separate for ease of understanding, however, these may be coaxial or otherwise arranged. The hand piece 112 includes portions of the irrigation system 335 and portions of the aspiration system 365. In addition, the hand piece 112 includes a pump 360 and a sensor 392 associated with the aspiration system 365. In some exemplary embodiments, the sensor 392 may be located along the aspiration path 375 or located near the distal end 310 and in fluid communication with the surgical site. In some embodiments, the sensor 392 may be located within the surgical site and in communication with a controller forming a part of the fluidics subsystem 110, as described below. In some embodiments, the sensor 392 detects a pressure at the surgical site or a pressure associated with the surgical site. In this exemplary embodiment, the hand piece 112 also includes an aspiration valve 390, which is shown associated with the aspiration system 365.

The irrigation system 335 includes an irrigation conduit 340 that forms an irrigation path 345 that is in fluid communication with the sleeve 325 and an irrigation fluid supply 350. Irrigation fluid 355 flows from the irrigation fluid supply 350, through the irrigation conduit 340 and through the sleeve 325 into the surgical site. The irrigation fluid supply 350 may be located, for example, on an intravenous pole at a fixed or adjustable height or otherwise disposed about the system. In one embodiment, the irrigation conduit 340 and the irrigation fluid supply 350 are not in contact with the base housing 102, therefore active irrigation is eliminated. The irrigation conduit 340 may be a flexible tubing. In the exemplary embodiment shown, the pump 360 interfaces with the flexible irrigation conduit 340. In some embodiments, the irrigation system 335 includes an optional irrigation sensor 342 that may be used to detect fluid characteristics of the irrigation fluid in the irrigation conduit 340. In one embodiment and as shown in FIG. 3, the optional irrigation sensor 342 is located along the irrigation path 345 between the driver 400 and the distal end 310. In another embodiment (not shown), the optional irrigation sensor 342 is located along the irrigation path 345 between the driver 400 and the proximal end 315. In one embodiment, the optional irrigation sensor 342 is a pressure transducer configured to detect pressure within the irrigation conduit 340. The pressure transducer may be configured to detect pressure upstream from the pump 360 and the detected pressure may be correlated to a flow rate. In embodiments where the pressure transducer is disposed to detect pressure downstream from the pump 360, the detected pressure may be correlated to a flow rate or may be correlated to pressure within the surgical site or may be correlated to IOP. In another embodiment, the optional irrigation sensor 342 is a flow sensor that directly measures flow in the irrigation conduit 340.

The aspiration system 365 includes an aspiration conduit 370 that forms an aspiration path 375 that is in fluid communication with the tip 320 and a drain reservoir 380. In some embodiments, the aspiration conduit 370 is a flexible tubing. Aspiration fluid 385 flows away from the surgical site, through the tip 320 and collects in the drain reservoir 380. The aspiration system 365 also comprises the aspiration valve 390. In some embodiments, the aspiration valve 390 is a variable controlled valve. In some embodiments, the aspiration valve 390 is a peizotronic valve. In the embodiment shown, the aspiration valve 390 is located between the pump 360 and the proximal end 315. In the exemplary embodiment shown, the pump 360 interfaces with the flexible aspiration conduit 370. Aspiration fluid 385 generally comprises irrigation fluid 355 that has been in contact with the surgical site, and other matter, such as an eye lens, that is to be removed from the surgical site.

In FIG. 3, the pump 360 simultaneously interfaces with both the irrigation conduit 340 and the aspiration conduit 370. The pump 360 comprises a motor 395 and a driver 400. In some embodiments, the pump 360 is a peristaltic pump. In one embodiment, the driver 400 has a spiral structure that presses against the flexible aspiration conduit 370 and the flexible irrigation conduit 340. In this manner, a screw-type or scroll-type aspiration pump is implemented with the motor 395, the driver 400, the aspiration conduit 370, and the irrigation conduit 340. The irrigation conduit 340 is disposed so that the movement of the driver 400 causes the irrigation fluid 355 to flow away from the irrigation fluid supply 350 and towards the surgical site while it simultaneously causes the aspiration fluid 385 to flow away from the surgical site and towards the drain reservoir 380. The motor 395 is coupled to the driver 400 and serves to rotate the driver 400. The motor 395 can be controlled to control the movement of the driver 400 as more clearly described below. The motor 395 is typically a DC motor but can be any type of motor or driver suitable for rotating the driver 400. While the pump 360 is described as a screw-type peristaltic pump, other types of pumps may also be used.

In FIG. 3, the fluidics subsystem 110 may also include a controller 405. In some embodiments, the controller 405 is disposed on the console 100. The controller 405 is in communication with the sensor 392 and the optional irrigation sensor 342 and is configured to receive IOP information from the sensor 392 or the optional irrigation sensor 342 or both. The controller 405 may include a processor and memory that may include an executable program for operating the aspiration valve 390, for operating the pump 360, and or detecting information received from the sensors 392, 342. The controller 405 may receive inputs from an operator or may include pre-stored optimum targets for the irrigation flow or the aspiration flow or both. These target and received inputs may be a single value or a range of values. In one embodiment, the controller 405 is a PID controller configured to control the aspiration valve 390 to mitigate pressure deviations.

In one example, the controller 405 may include one or more pre-established optimum flow thresholds establishing desired fluid flow in the aspiration conduit 370, or the irrigation conduit 340, or both. The controller 405 may include an optimum irrigation flow threshold that is a function of an irrigation pressure or irrigation fluid flow rate. The controller 405 may include an optimum aspiration flow threshold that is a function of an aspiration pressure or aspiration fluid flow rate. Similar thresholds may be included for a pressure setting and a vacuum setting. These thresholds may be input by an operator or may be preset and stored during manufacturing.

The controller 405 is in communication with the pump 360 and is configured to control the operation of the pump 360. In operation, the motor 395 rotates the driver 400. The controller 405 controls the operation of the motor 395. In this manner, the driver 400 may be rotated at any desired speed to produce any desired aspiration flow and irrigation flow. When rotated, the driver 400 draws the aspiration fluid 385 through the aspiration conduit 370, and draws the irrigation fluid 355 through the irrigation conduit 340 towards the surgical site. The controller 405 uses the pressure information received from the sensor 392 or the optional irrigation sensor 342 or both to determine whether the speed of the pump 360 should be increased or decreased to maintain or regulate IOP.

The controller 405 is in communication with the aspiration valve 390 and is configured to control the state of the aspiration valve 390, meaning the controller controls the valve to move to a more open position, a fully open position, a more closed position, or fully closed position. In some embodiments, the flow of the aspiration fluid 385 is controlled by the state of the aspiration valve 390. The more open the aspiration valve 390, the higher the flow of the aspiration fluid 385 within the aspiration conduit 370. The less open the aspiration valve 390, the lower the flow of the aspiration fluid 385 within the aspiration conduit 370. The controller 405 uses the pressure or flow information received from the sensor 392 to determine whether the state of the aspiration valve 390 should be adjusted (increased or decreased). The controller 405 may be configured to control the IOP using any of a plurality of different or overlapping methods. Some embodiments employ the pump 360 in the hand piece to maintain a desired pressure or a desired flow to the eye. In one embodiment, the controller 405 is configured to maintain IOP by operating the pump at pre-established speed settings that correspond to particular flow rates through the irrigation conduit 340. Accordingly, to increase or decrease the flow rates to a desired target flow rate, the controller 405 controls the pump speed. In other embodiments, the controller 405 receives detected information from the optional irrigation sensor 342, and based on this information, the controller 405 is a responsive system that increases or decreases the pump speed to achieve the desired flow rate.

Other embodiments employ the valve 390 in the hand piece to maintain a desired pressure or a desired flow to the eye. In these embodiments, with the pump speed held constant, the controller 405 may control the valve 390 to increase or decrease the flow through the aspiration conduit 370. In some embodiments, the controller 405 operates the valve 390 to maintain aspiration fluid flow within a desired or target flow rate. This may be done by detecting a pressure or the flow rate in the aspiration conduit 370 with the sensor 392, and controlling the valve 390 to increase or decrease the flow rate through the valve 390. In some embodiments, the controller 405 operates the valve 390 based on valve position, where the flow rate is known based on the position on the valve 390. Accordingly for any given flow rate, the system may maintain the flow rate within a target range by setting the valve to a state that corresponds with the desired flow rate.

Yet other embodiments employ both the pump 360 and the valve 390 to achieve the desired flow rates, and likewise, the corresponding desired IOP. For example, a faster response may be achieved by simultaneously controlling both the pump speed and the valve state to increase or decrease flow in a manner to maintain a desired IOP.

In one embodiment, the body 305 includes an opening configured to receive a removable hand piece cartridge 406. The removable cartridge 406 comprises a portion of the irrigation system 335 and the aspiration system 365, with the portions of the irrigation system 335 and aspiration systems 365 being in fluid communication with the tip 320 and the sleeve 325. The use of a removable hand piece cartridge 406 eliminates the need for fluidic cassettes that are generally attached to or within the base housing 102 of the console 100. The removable cartridge 406 may be snapped into place to selectively engage with the pump. In some embodiments, the removable cartridge is for a one-time use.

In one embodiment, the length of aspiration conduit and irrigation conduit between the pump 360 and the surgical site is minimal (on the order of inches or centimeters). In addition, this length of aspiration conduit and irrigation conduit between the pump and the surgical site may be non-compliant (i.e., it can be rigid). This is represented in FIG. 3 by the length of conduit 407. Having a small length of non-compliant conduit 407 between the pump 360 and the surgical site may relieve post-occlusion surge associated with prior art systems.

The cross-sectional areas of the irrigation and aspiration conduits 340, 370 may be selected to provide a desired flow rate. In some embodiments, a cross sectional area of the irrigation conduit 340 and a cross sectional area of the aspiration conduit 370 are the same. In other embodiments, the cross-sectional areas are different. In one embodiment, the cross sectional area of the irrigation conduit 340 may be larger than the cross sectional area of the aspiration conduit 370 in order to achieve an irrigation fluid flow that is greater than the aspiration fluid flow, thereby ensuring that the irrigation fluid flow is greater than the aspiration fluid flow. Due to the irrigation conduit 340 and aspiration conduit 370 both interfacing with the driver 400 of the motor 395, differing the cross sectional areas allows for the same driver rotation to produce a variety of irrigation fluid flow to aspiration fluid flow ratios.

In the exemplary embodiment shown in FIG. 3, the pressure sensor 392 is located along the aspiration path 375 between the pump 360 and the distal end 310. In this manner, the sensor 392 can accurately read the pressure conditions in the aspiration conduit 370 very close to the surgical site. Detecting pressure conditions close to the surgical site results in early detection of occlusion breaks, and therefore, allowing for early response to prevention of occlusion surges. In some embodiments (not shown), the pressure sensor 392 is located along the aspiration path 375 between the pump 360 and the proximal end 315.

In another embodiment, the irrigation system 335 includes an optional shunt line and irrigation valve 396 (shown in dashed lines), which may be a variable controlled valve. In one embodiment, the valve is a peizotronic valve. However other valves also may be used. The valve 396 may be used to bleed irrigation fluid downstream from the pump to the aspiration line downstream of the aspiration valve 390. The valve 396 also may be controlled by the controller and may be adjusted to affect fluid flow through the irrigation line. For example, the valve 396 may be opened to permit fluid flow to continue through the irrigation line when the aspiration valve is closed to affect IOP. This may also reduce the likelihood of an IOP spike when the aspiration valve 390 is controlled.

Figure 4:
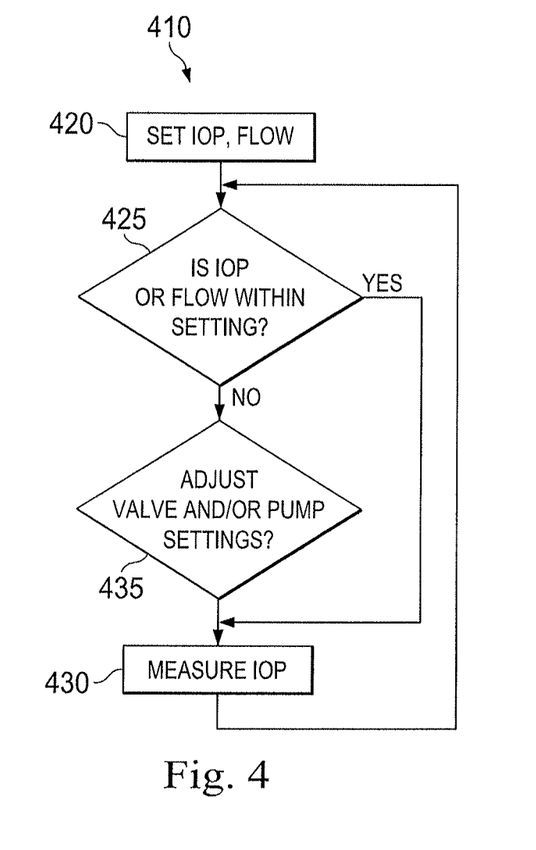
FIG. 4 is flow chart illustration of a method of operating the phacoemulsification hand piece of FIG. 3, according to an embodiment consistent with the principles of the present disclosure.

FIG. 4 illustrates an exemplary method of operating the fluidics subsystem 110. The method is generally referred to by the reference number 410. Using the method 410, the fluidics subsystem 110 may detect pressure deviations in the system, such as those that may occur as a result of an occlusion surge, and may quickly act to counter the effects of the occlusion surge. For example, the fluidics subsystem 110 may use the information from the sensor 392 to detect clogged tips due to changes in pressure, as an indicator of the IOP in the eye. Upon detecting a clog (based on the pressure readings or IOP information from the sensor 392), aspiration and irrigation flows can be adjusted using the pump 360 and the aspiration valve 390, to reduce the effects of a post-occlusion surge. The continuous detection of the IOP information by the sensor 392 may result in a more consistent and predictable phacoemulsification procedure by reducing the effects of pressure deviations that occur with post-occlusion surges. That is, by immediately responding to the deviations in pressure.

Referring to FIG. 4, at a step 420, the surgeon sets a target IOP on the console and/or a desired flow. The controller 405 activates the pump 360 to cause the irrigation fluid 355 to flow through the irrigation conduit 340 and the aspiration fluid 385 to flow through the aspiration conduit 370.

At a step 425, the controller 405 receives information from the aspiration sensor 392 and determines whether the IOP is at the set IOP of within a range of the set IOP. From this, the system may calculate, or may also directly measure, the flow. If the IOP is within the desired range, the system continues to measure IOP as indicated at step 430. It should be noted that the optimum irrigation flow may be either a specific target value or may be a range of values. If the IOP is outside the desired range, then the system adjusts the pump valve setting to alter the flow at a step 435, thereby directly influencing the IOP. The pump valve adjustment may be done to either increase the flow or to decrease the flow based on the measurement taken. In some embodiments, the system also adjusts the setting on the optional irrigation valve 396 to permit at least a portion of the irrigation fluid to bypass the IOP to reduce the likelihood of an IOP spike.

In conventional phacoemulsification systems, the pump is located within the base housing 102. A relatively long length of flexible conduit (six feet or more) is located between an aspiration and irrigation pump and the eye. This relatively long length of flexible conduit has a lot of compliance—it can stretch in response to changes in vacuum pressure. This compliance can result in surges as previously described. By incorporating the pump that interfaces with both the irrigation conduit and the aspiration conduit in the hand piece 112 (and placing it very close to the eye) and having a very short length of non-compliant conduit 407 between the pump 360 and the eye, the effects of these surges can be reduced or eliminated, thus resulting in a more consistent and predictable surgery. The system disclosed herein, with the hand piece pump 360 that drives both the irrigation and the aspiration may decrease conduit compliance, decrease pump control delay times, may decrease irrigation resistance to flow, and/or may decrease other delays that might result from using a pressure transducer far down stream in a fluidics cassette. Additionally, because the pump 360 interfaces with the irrigation conduit 340 and causes the irrigation fluid 385 to flow through the irrigation path 375, active irrigation or the pumping of irrigation fluid from the base housing 102, is no longer needed. In addition, some components are eliminated or replaced by this system, such as a fluidics cassette and an active irrigation system.

In one embodiment however, a single-use, removable hand piece cartridge of the hand piece 112 may replace the fluidics cassette which, in conventional systems, is temporarily placed in the base housing 102. Instead, the irrigation conduit may be directly connected from the hand piece 112 to the irrigation fluid supply 350, which can be located at a fixed bottle height.

Persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A surgical system comprising:
   a hand piece;
   an aspiration conduit;
   an irrigation conduit;
   a pump disposed within the hand piece, wherein at least a portion of the pump interfaces with the aspiration conduit and the irrigation conduit, such that upon activation of the pump, the irrigation fluid within the irrigation conduit flows in a direction towards the surgical site, and the aspiration fluid within the aspiration conduit flows in a direction away from the surgical site;
   an aspiration valve disposed within the hand piece and in the aspiration conduit between the pump and a drain reservoir;
   a sensor configured to detect a pressure at or along the aspiration conduit or the irrigation conduit; and
   a controller in communication with the pump, the aspiration valve, and the sensor;
   wherein the controller is configured to control the operation of the pump and the aspiration valve based on information from the aspiration sensor.

2. The system of claim 1, wherein the controller is configured to change IOP by adjusting a pump speed or by adjusting a state of the aspiration valve or both.

3. The system of claim 1, wherein the sensor is located within the hand piece along the irrigation conduit or along the aspiration conduit.

4. The system of claim 1, wherein the irrigation conduit comprises a first cross-sectional area and the aspiration conduit comprises a second cross-sectional area, the first cross-sectional area being larger than the second cross-sectional area.

5. The system of claim 1, wherein the hand piece further comprises:
   a removable cartridge disposed in the body having at least a portion of the aspiration conduit and/or at least a portion of the irrigation conduit.

6. The system of claim 1, comprising a second valve controlling flow through a line connecting the irrigation line to the aspiration line.

7. The system of claim 6 wherein the controller controls IOP by adjusting a state of the second valve.

8. A surgical system comprising:
   a hand piece;
   an aspiration conduit;
   an irrigation conduit;

a shunt line fluidly coupled at a proximal end to the irrigation conduit and fluidly coupled at a distal end to the aspiration conduit;

a pump disposed within the hand piece, wherein at least a portion of the pump interfaces with the aspiration conduit and the irrigation conduit, such that upon activation of the pump, the irrigation fluid within the irrigation conduit flows in a direction towards the surgical site, and the aspiration fluid within the aspiration conduit flows in a direction away from the surgical site;

an aspiration valve disposed within the hand piece and in the aspiration conduit between the pump and a drain reservoir;

an irrigation valve located in the shunt line;

an aspiration sensor detecting an aspiration pressure at or along the aspiration conduit;

an irrigation sensor detecting an irrigation pressure at or along the irrigation conduit; and a controller in communication with the pump, the aspiration valve, the aspiration sensor, the irrigation valve, and the irrigation sensor;

wherein the controller is configured to control the operation of the pump, the aspiration valve, and the irrigation valve based on information from the aspiration sensor and/or the irrigation sensor.

9. The system of claim 8, wherein the controller is configured to change IOP by any combination of the following: adjusting a pump speed, adjusting a state of the irrigation valve, adjusting a state of the aspiration valve.

10. The system of claim 8, wherein the irrigation conduit comprises a first cross-sectional area and the aspiration conduit comprises a second cross-sectional area, the first cross-sectional area being larger than the second cross-sectional area.

11. The system of claim 8, wherein the hand piece further comprises:

a removable cartridge disposed in the body having at least a portion of the aspiration conduit and/or at least a portion of the irrigation conduit.

* * * * *

UNITED STATES PATENT AND TRADEMARK OFFICE
CERTIFICATE OF CORRECTION

PATENT NO. : 10,182,940 B2
APPLICATION NO. : 15/239409
DATED : January 22, 2019
INVENTOR(S) : Chandrakant et al.

It is certified that error appears in the above-identified patent and that said Letters Patent is hereby corrected as shown below:

On the Title Page

Item (73) Assignee: "Novartis AG" should read --Alcon Research, Ltd.--.

Signed and Sealed this
Twenty-ninth Day of October, 2019

Andrei Iancu
*Director of the United States Patent and Trademark Office*